United States Patent
Danyluk et al.

(10) Patent No.: US 6,253,619 B1
(45) Date of Patent: Jul. 3, 2001

(54) ADJUSTABLE ACOUSTIC MIRROR

(75) Inventors: Michael J. Danyluk, Cincinnati; Richard E. Klaassen, West Chester; Michael E. Keller, Mason, all of OH (US)

(73) Assignee: General Electric Company, Cincinnati, OH (US)

( * ) Notice: Subject to any disclaimer, the term of this patent is extended or adjusted under 35 U.S.C. 154(b) by 0 days.

(21) Appl. No.: 09/377,416

(22) Filed: Aug. 20, 1999

(51) Int. Cl.[7] .................................................. G01N 29/04
(52) U.S. Cl. ............................................. 73/642; 73/601
(58) Field of Search ........................... 73/601, 618, 620, 73/642, 643, 641; 367/7, 150, 151, 138

(56) References Cited

U.S. PATENT DOCUMENTS

| | | | | |
|---|---|---|---|---|
| 3,622,790 | * | 11/1971 | Zavodny | 250/199 |
| 3,927,557 | * | 12/1975 | Viertl | 73/67.5 R |
| 4,269,067 | * | 5/1981 | Tynan et al. | 73/643 |
| 4,606,031 | * | 8/1986 | Beene et al. | 372/28 |
| 5,240,005 | * | 8/1993 | Viebach | 128/663.01 |
| 5,596,989 | * | 1/1997 | Morita | 128/660.1 |
| 5,677,491 | * | 10/1997 | Ishrak et al. | 73/641 |
| 5,680,863 | * | 10/1997 | Hossack et al. | 128/662.03 |
| 5,859,417 | * | 1/1999 | Dvorkis et al. | 235/467 |

FOREIGN PATENT DOCUMENTS

| | | | |
|---|---|---|---|
| 58-017361 | * | 2/1983 | (JP) . |
| 5-134688 | * | 5/1993 | (JP) . |

* cited by examiner

Primary Examiner—Helen Kwok
(74) Attorney, Agent, or Firm—Andrew C. Hess; Gerry S. Gressel

(57) ABSTRACT

An ultrasonic inspection element and method are provided for improved ultrasonic inspection of curved entry surface parts. The transducer element may be spherically focused, or have a flat surface. The transducer/mirror element combination is used to inspect through a concave or convex surface. A mirror element shapes the sound beam relative to the shape of the curved surface of the part being inspected. Curvature of the mirror is adjusted with a screw, rod, voltage modulator, or other suitable adjustment mechanism. An alternative mechanism includes multiple "quick disconnect" interchangeable curved mirror elements.

19 Claims, 5 Drawing Sheets

ADJUSTABLE ACOUSTIC MIRROR

BACKGROUND OF THE INVENTION

The present invention relates to ultrasonic inspection and particularly to an adjustable acoustic mirror for improving ultrasonic inspection through curved surfaces.

When an ultrasonic inspection is performed, a transducer is calibrated on a flat-top block made from the same material as that being inspected, and containing flat bottomed holes of known diameter and known depth from the surface. A set of inspection parameters, such as energy level, operating frequency and water-path, are set and calibrated to a flat-top block calibration standard. The inspection parameters are used to inspect production hardware. In many cases, the same block inspection parameters are used to inspect through curved entry surfaces. Conventional procedure provides that certain curved surface parts with entry surface curvature larger than about 38 cm radius are inspected just like flat-top parts. For radii less than 38 cm, typically the operator will increase the gain (energy level). This compensates for losses due to the curved entry surface. Increasing the gain, however, also increases both the system noise (electronic noise) and the material noise, and for a large number of aircraft engine materials the parts become "uninspectable" (the part fails inspection because of "high noise", i.e. "noise rejects"). The problem is escalated when trying to focus a sound beam below the curved entry surface (subsurface focusing), and, is more pronounced when going through a concave surface than through a convex surface.

Passing a sound beam through a curved surface decreases the effective sensitivity. A concave surface will cause the beam to focus much shorter than the operator expects. A convex surface will defocus the beam, yielding a less sensitive sound beam than the operator expects and that may not ever focus. The severity of each case is dependent on the radius of curvature of each, the smaller (or tighter) the radius the greater the effect on the sound beam. Also, for surfaces with curvature in just one direction, such as a bore or hole for example, the sound beam will not focus since the surface is not symmetric about the center of the transducer beam. The effect of a curved surface on inspection sensitivity is very complex. It is therefore difficult to compensate for the effect of curved surfaces without some form of correction. Such a correction would keep the same sensitivities and beam properties as those of the flat entry surface. Currently, curved parts receive additional inspection gain to compensate for the energy loss at the material boundary. The inspection gain is determined for each radius and inspection depth combination.

Improving ultrasonic inspection capabilities through curved surfaces has been an insurmountable obstacle for many years. Curved surfaces redirect the sound beam, often in an undesirable direction, resulting in loss of energy and resolution. The severity of the incorrect focusing and energy loss is dependent on the magnitude of the surface curvature. The more curvature there is, the more incorrect focusing, energy loss, and resolution loss there will be. Hence, even providing a fixed curvature acoustic mirror for inspection will not be wholly accurate for all curvatures.

An adjustable or precisely interchangeable device is desired, capable of accurately inspecting any curved surface, regardless of its curvature.

BRIEF SUMMARY OF THE INVENTION

Mathematical calculation shows that concave surfaces, not just convex, need compensation to get inspection results like a flat surface. However, concave surfaces present complications in that intensity of the sound beam increases then, after a certain depth, sharply decreases. The radius of the surface determines the change in both intensity and depth. For example, in a bore (one concave radius of curvature) the sound energy is split. The portion of the beam entering the plane of the curved surface is focused shallower than the portion entering the plane of the flat surface. Hence, an adjustable acoustic mirror or a fixed shape interchangeable mirror is provided. The mirror improves ultrasonic inspection through concave and convex curved surfaces, regardless of the curvature.

An ultrasonic inspection element and method are provided for ultrasonic inspection. The system for use with a transducer inspects through a curved surface. The transducer has a spherically focused lens. A mirror element is provided for shaping the sound beam. Curvature of the mirror is adjusted with an adjustment means such as a screw, rod, or voltage modulator. An alternative means to change the mirror curvature is to interchange fixed curvature mirror elements. All segments of the mirror elements can be fashioned as "quick disconnect" units. This allows efficient, repeatable assembly of a complete inspection system.

Accordingly, the present invention provides an effective technique for performing ultrasonic inspection, particularly of curved surface parts.

DETAILED DESCRIPTION OF THE INVENTION

Figure 1:
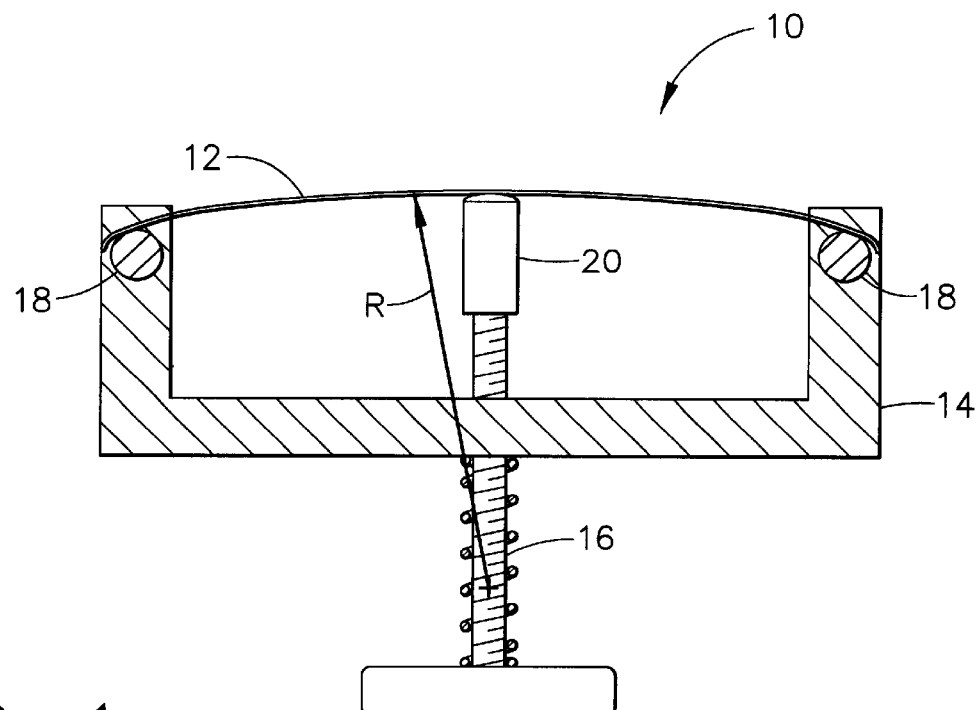
FIG. 1 illustrates an adjustable curvature structure of a mirror, by translational movement of an adjustment screw in a three-point bend configuration.

The present invention proposes an acoustic mirror for ultrasonic inspection through any curved surface. The mirror will inspect through concave radii of virtually any dimension, including rotating parts inspected with ultrasound. The mirror can also be used for subsurface-focus ultrasonic inspection in materials having a preferred ultrasonic direction. Such materials exhibit beam steering phenomena. For example, single crystalline materials and laminate composite materials are such materials. These materials steer sound energy in a direction that is dependent on the structure of the material. In a single crystalline material, the sound energy is directed, or steered, in a path along the primary crystallographic axis. In a laminate composite material, the sound energy is directed in a path along the fiber axis. The adjustable acoustic mirror, or the fixed curvature interchangeable mirror elements, can compensate for the natural steering effects in materials.

Referring to the drawings, an acoustic mirror 10 improves ultrasonic inspection through curved surfaces. The mirror 10 comprises a flexible mirror element 12 in a mirror frame structure 14. The mirror element 12 may be any suitable thickness as determined by transducer frequency, acoustic impedance and flexibility of the mirror material. For example, the mirror element 12 would need to be around 0.038 cm thick piece of stainless steel for transducers that are 5–50 MHz. For transducers less than 5 MHz, the mirror element 12 would need to be thicker than 0.038 cm if stainless steel is to be used. A means 16, such as an adjustment screw, adjusts the flexible mirror element 12 depending on the curvature being inspected. This adjustability allows the mirror 10 to focus sound energy through a variety of concave and convex surfaces.

Figure 3:
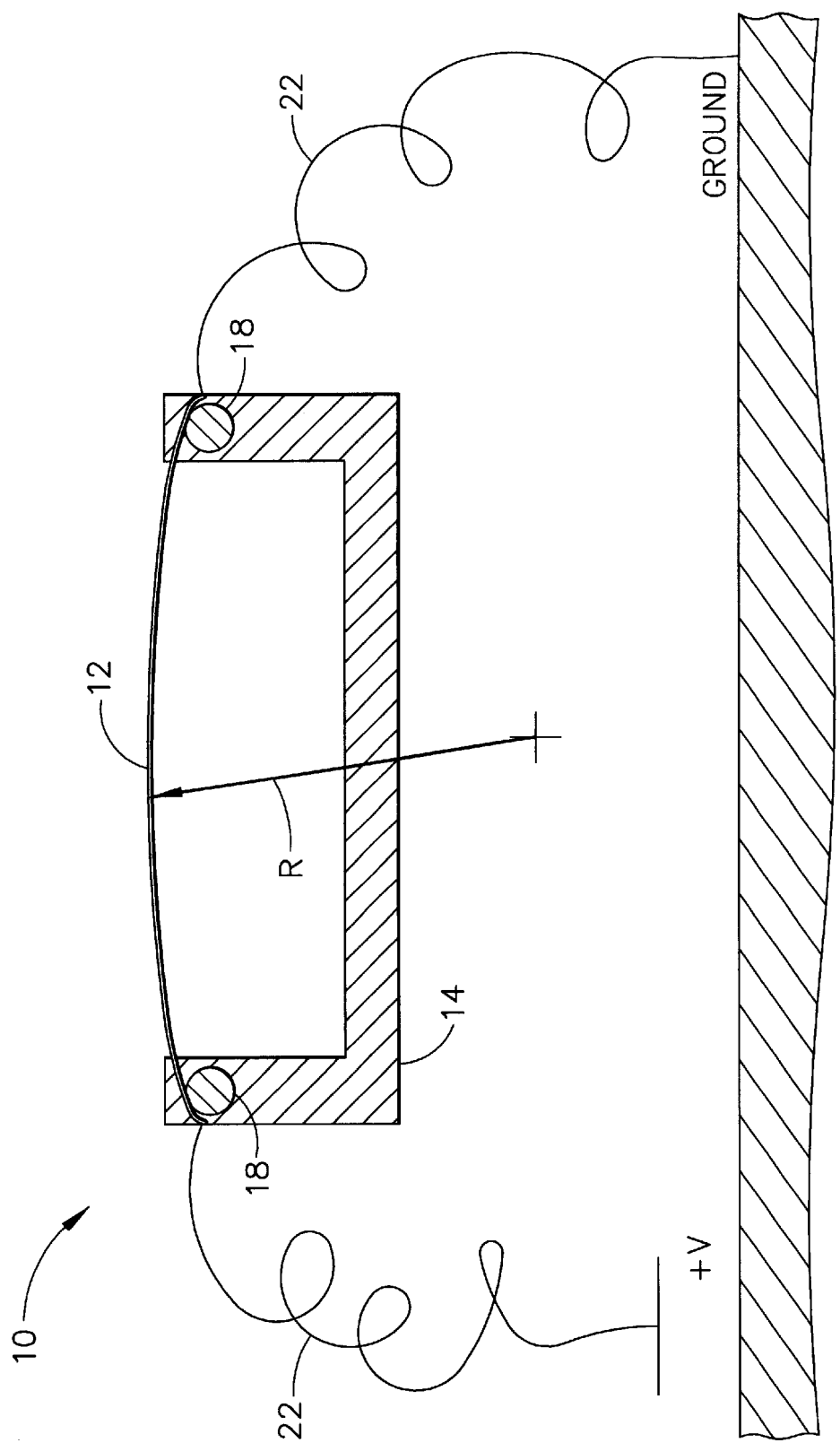
FIG. 3 illustrates an adjustable curvature structure of a mirror, by modulating voltage to a reflective piezoelectric element.

Curvature of the mirror element 12 is controlled in FIG. 1 using a mechanical three-point bend configuration. The three points are the two ends 18 where the mirror element is attached, and the screw/beam contact point 20. The means 16 may also be a voltage source, and the mirror element can be a piezoelectric material, as in FIG. 3. In this case, curvature is induced from the voltage along 22. That is, the mirror element 12 changes shape with voltage. Modulating the voltage can control the mirror 12 curvature. The mirror element 12 is constrained in the vertical direction, and is allowed to rotate and translate in the horizontal direction about the fixed ends, 18, attached to mirror frame 14. The adjustment means 16 is used to regulate mirror curvature, and the beam insures uniform curvature to the mirror element. The actual adjustment of means 16 can be manual or motorized. And, if the mirror element 12 is made from a piezoelectric material, as shown in FIG. 3, a voltage is applied. Then the mirror element becomes the means as well, capable of adjusting the mirror curvature.

Figure 2:
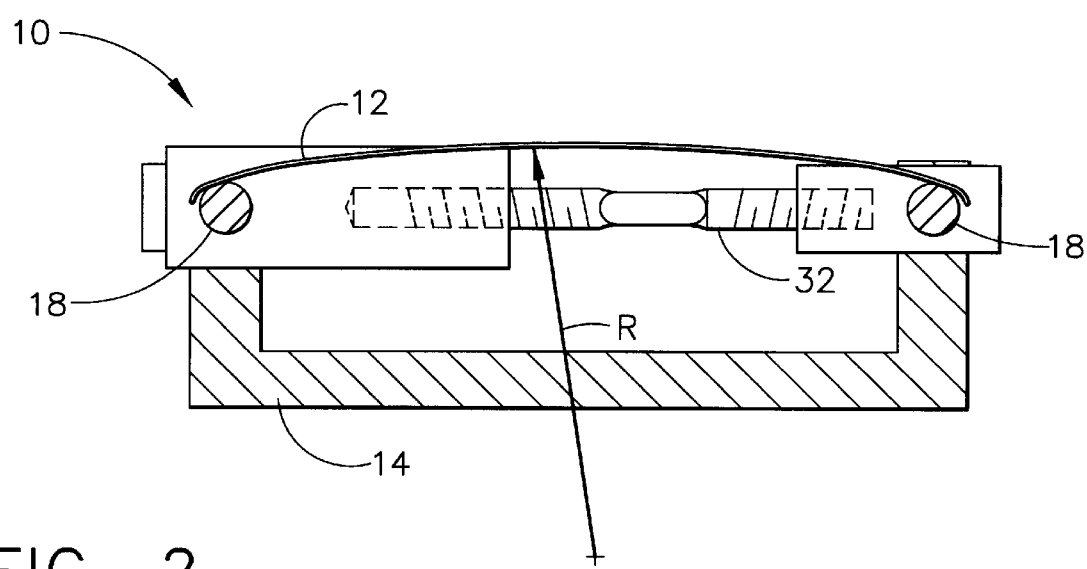
FIG. 2 illustrates an adjustable curvature structure of a mirror, by horizontal bi-directional movement of an adjustment rod in a compression mode.

As stated, the mirror element may be a single adjustable mirror, or multiple interchangeable units. With the adjustable mirror element 12, as illustrated in FIGS. 1 and 2, the adjustment means 16 can be any suitable means. For example, in FIG. 2, the adjustment is a rod 32, which can comprise one or multiple rods. The adjustment rod 32 controls mirror curvature with movement between the ends, compressing the distance. The type of mirror, concave or convex, is determined by whether the element is deflected up (convex mirror) or down (concave mirror). A convex mirror would most likely be used on a concave surface. A concave mirror would most likely be used on a convex surface. In both cases, the adjustment rod 32 compresses the distance. Each end 18 can be moved simultaneously; or differently to create the desired curvature of mirror 12. Movement may also be in both directions simultaneously or each direction independently along an approximate horizontal axis of mirror 12. An advantage of the configuration of FIG. 2 is that each turn buckle rod 32 may be adjusted independently. This allows for more flexible mirror shapes, such as cone, tapered holes, and some compound curvatures, where there is a different radius 90 degrees apart. The embodiment in FIG. 1 allows curvature adjustment in just one plane (hence, the name cylindrical mirror). The embodiment in FIG. 2 allows for a cone shape as well as a cylindrical shape.

Figure 4:
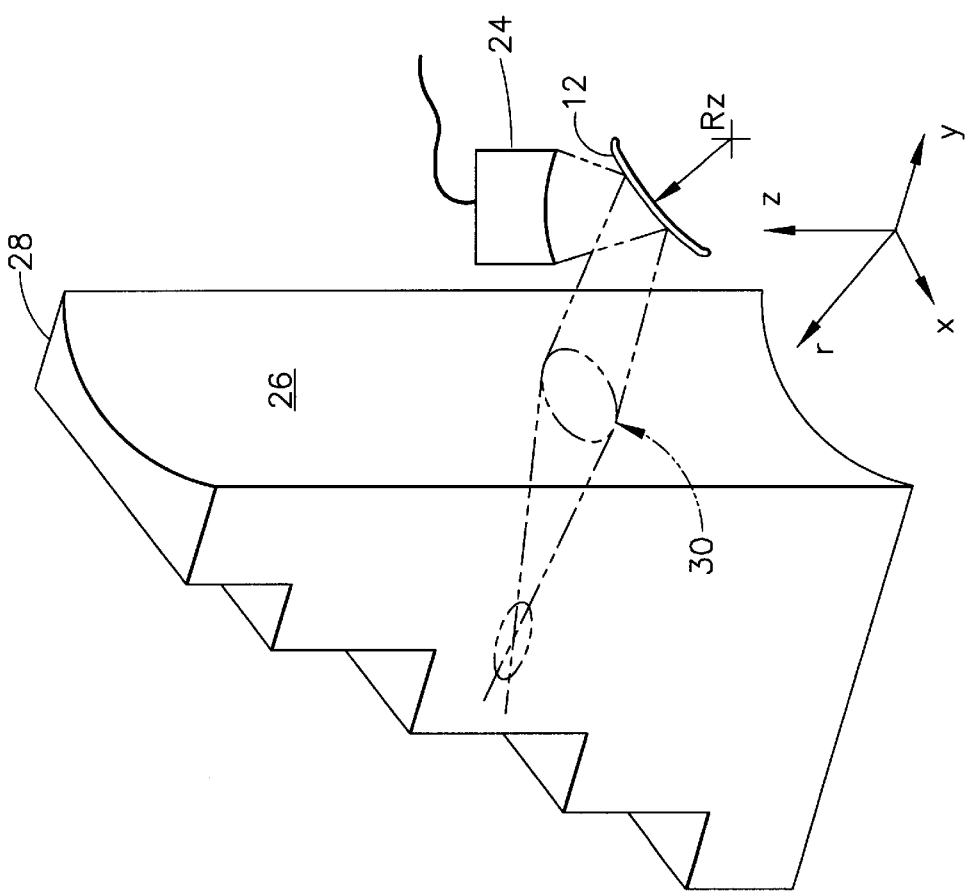
FIG. 4 illustrates one example of the relative positioning of an adjustable curvature mirror to a curved surface part with curvature in just one direction.

As illustrated in FIG. 4, the mirror element 12 is oriented at around 45 degrees with respect to transducer 24 axis. The transducer may be placed generally one inch or more above the mirror surface. In FIG. 4, the transducer-mirror apparatus 12, 24, is being used to inspect curved surface 26 of part 28, a step-block. The entry surface cone 30 resembles an ellipse 30. The curvature of mirror 12 is adjusted to shape the sound beam.

FIG. 4 shows the relative location and orientation of the mirror/transducer apparatus. The step block is an example of a "calibration block". This block has Flat Bottom Holes (FBHs) drilled at specific depths below the surface. Calibration is made off of these holes, then the production part is inspected to that sensitivity. The step block is the same shape (as to radius and acoustic properties) as a production part. It is used to develop/setup/measure an inspection.

Figure 7:
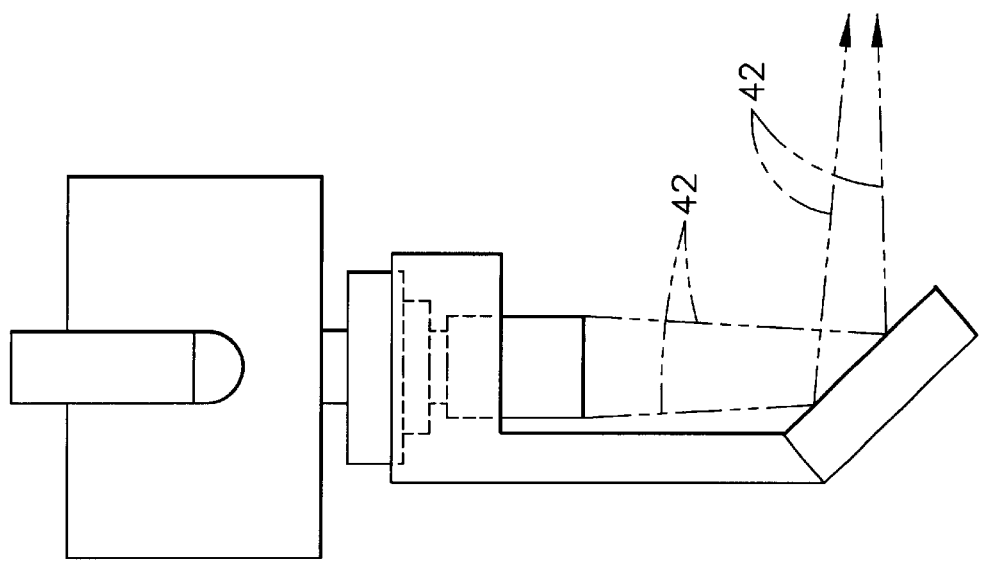
FIGS. 5, 6 and 7 illustrate a quick-coupler, detachable structure that can support both adjustable and nonadjustable (fixed) curvature mirrors.
Figure 6:
Figure 5:
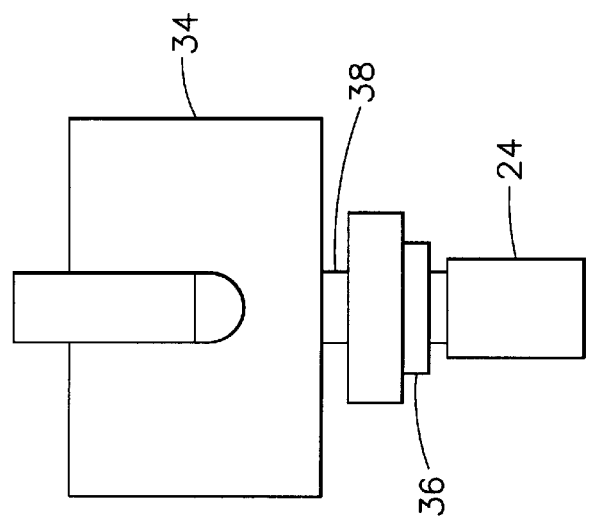

FIGS. 5, 6 and 7 illustrate a quick-coupler, detachable structure that can support both adjustable and nonadjustable (fixed) curvature mirrors. These drawings show how the interchangeable mirror element sits relative to the transducer 24 and a manipulator head 34. In FIG. 5, a quick-coupler mirror collar 36 can use dowel pins to insure alignment. The collar 36 is aligned once during installation and is tightened around an UHF connector 38 associated with manipulator head 34.

In FIG. 6, a quick-coupler, detachable mirror holder 40 can support the mirror element 12, whether flat or curved, interchangeable or adjustable. It may be used in any ultrasonic inspection where a flat or curved 45-degree mirror is needed. The mirror holder 40 is preferably stainless steel or PVC. Guide slots (not shown) in the holder can be fitted to dowel pins on the collar 36. As illustrated in FIG. 7, the beam focal properties, indicated by lines 42, are affected by the mirror element curvature.

Figure 9:
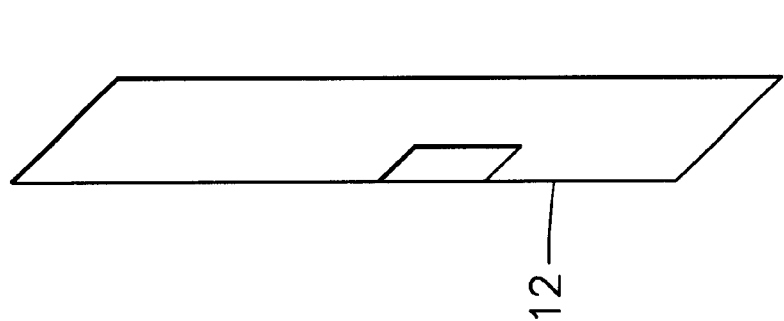
FIGS. 8 and 9 illustrate a top and side view, respectively, of the interchangeable fixed curvature mirror elements.
Figure 8:
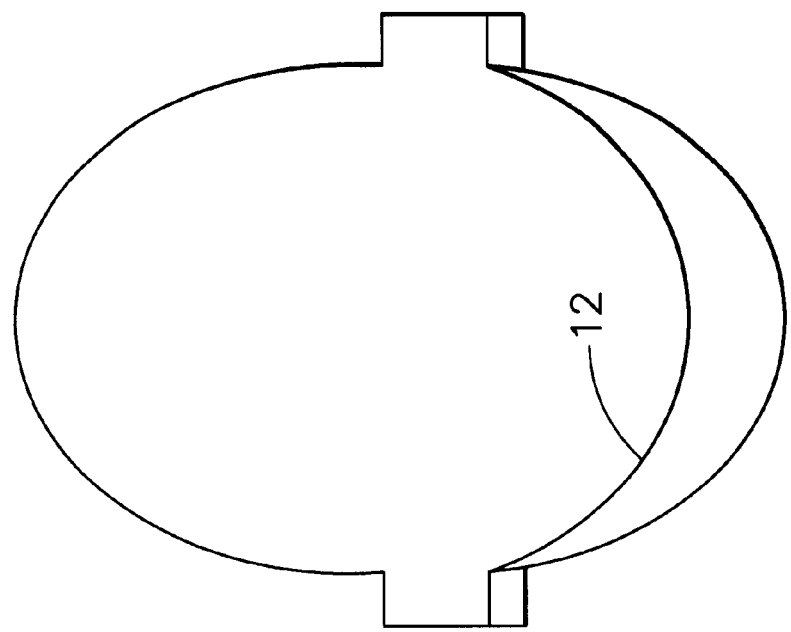

Representative fixed mirror element examples are illustrated in FIGS. 8 and 9. FIG. 8 illustrates a top view of the fixed mirror element 12, and FIG. 9 illustrates a side view. The interchangeable mirror elements 12 can be flat or curved. Curved mirror elements will change the beam focal properties.

While the invention has been described with reference to a preferred embodiment, it will be understood by those skilled in the art that various changes may be made and equivalents may be substituted for elements thereof without departing from the scope of the invention. For example, this process can be applied in various environments such as turbine blades with laser drilled holes. The process can also be applied to any part that has laser expulsion on its surface and around the hole. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for improving ultrasonic inspection through a curved surface, comprising the steps of:

provided a mirror element for shaping a sound beam of the ultrasonic inspection; and adjusting curvature of the mirror element relative to the curved surface regardless of whether the curved surface is concave or convex.

2. A method as claimed in claim 1 wherein the mirror element comprises a single adjustable acoustic mirror.

3. A method as claimed in claim 2 wherein the step of adjusting curvature of the mirror element comprises the step of changing the curvature of the adjustable acoustic mirror.

4. A method as claimed in claim 3 wherein the step of changing the curvature comprises the step of using a screw.

5. A method as claimed in claim 3 wherein the step of changing the curvature comprises the step of using at least one rod.

6. A method as claimed in claim 1 wherein the mirror element comprises a piezoelectric mirror.

7. A method as claimed in claim 6 wherein the step of adjusting curvature of the mirror element comprises the step of using a voltage modulator.

8. A method as claimed in claim 1 wherein the mirror element comprises multiple interchangeable mirrors, each having a fixed curvature on at least one side.

9. A method as claimed in claim 8 wherein the multiple interchangeable mirror elements are each changed and locked in place by sliding over a spring-loaded tensioner.

10. A method as claimed in claim 8 wherein each multiple interchangeable mirror element is mechanically locked in place.

11. A method as claimed in claim 8 wherein each multiple interchangeable mirror element is used with a transducer to create a transducer-mirror assembly.

12. A method as claimed in claim 11 wherein the transducer-mirror assembly is detached and reattached to a manipulator head by a cylindrical interconnect.

13. A method as claimed in claim 11 wherein the transducer-mirror assembly is mechanically detached and reattached to the manipulator head.

14. A method as claimed in claim 11 wherein at least part of the transducer-mirror assembly comprises lightweight plastic.

15. A method as claimed in claim 11 wherein each of the multiple interchangeable mirror elements are detachable and attachable using precise, repeatable positioning.

16. A method as claimed in claim 11 wherein the transducer comprises a transducer having a spherically focused lens.

17. A method as claimed in claim 11 wherein the transducer comprises a transducer having a flat lens.

18. A method for improving ultrasonic inspection through a curved surface, comprising the steps of:
   providing a single acoustic adjustable mirror element for shaping a sound beam of the ultrasonic inspection; and
   adjusting curvature of the mirror element relative to the curved surface regardless of whether the curved surface is a concave surface or a convex surface.

19. A method for improving ultrasonic inspection through a curved surface, comprising the steps of:
   providing a plurality of curved mirror elements for shaping a sound beam of the ultrasonic inspection; and
   interchanging the plurality of curved mirror elements to adjust curvature of each of the mirror elements relative to the curved surface regardless of whether the curved surface is a concave curved surface or a convex curved surface.

* * * * *